United States Patent
Ortega, II et al.

(10) Patent No.: US 6,322,776 B1
(45) Date of Patent: Nov. 27, 2001

(54) ANHYDROUS HIGH-SPF ULTRAVIOLET LIGHT SCREENS

(75) Inventors: Alejandro V. Ortega, II, Jersey City; John A. Scott, Succasunna, both of NJ (US)

(73) Assignee: Schering-Plough HealthCare Products, Inc., Memphis, TN (US)

( * ) Notice: Subject to any disclaimer, the term of this patent is extended or adjusted under 35 U.S.C. 154(b) by 0 days.

(21) Appl. No.: 09/596,393

(22) Filed: Jun. 16, 2000

Related U.S. Application Data

(60) Provisional application No. 60/140,047, filed on Jun. 18, 1999.

(51) Int. Cl.$^7$ ................................ A61K 7/42; A61K 7/00
(52) U.S. Cl. .............................................. 424/59; 424/401
(58) Field of Search .................................. 424/59, 401, 60

(56) References Cited

U.S. PATENT DOCUMENTS

| | | | |
|---|---|---|---|
| 5,116,604 | * 5/1992 | Fogel et al. | 424/59 |
| 5,676,934 | * 10/1997 | Siegfried | 424/59 |
| 6,074,630 | * 6/2000 | Devillez et al. | 424/59 |
| 6,103,221 | * 8/2000 | Arnaud et al. | 424/59 |

* cited by examiner

*Primary Examiner*—Shelley A. Dodson
*Assistant Examiner*—Michael A. Williamson
(74) *Attorney, Agent, or Firm*—Robert A. Franks

(57) ABSTRACT

The invention relates to anhydrous compositions that are useful as UV-light screens for mammalian skin. Such compositions comprise octocrylene, octyldodecyl neopentanoate, and a $C_1$–$C_4$ alcohol vehicle. The invention also relates to methods of inhibiting or preventing UV light-induced skin damage by administering an effective amount of such a composition to the skin of a mammal in need of such inhibition or protection.

20 Claims, No Drawings

US 6,322,776 B1

ANHYDROUS HIGH-SPF ULTRAVIOLET LIGHT SCREENS

CROSS-REFERENCE TO RELATED APPLICATION

This application claims benefit under 35U.S.C. §119 from provisional application Ser. No. 60/140,047 filed Jun. 18, 1999.

BACKGROUND OF THE INVENTION

This invention relates to novel, anhydrous compositions that are useful as ultraviolet-light ("UV-light") screens for mammalian skin. This invention also relates to methods of inhibiting or preventing UV light-induced skin damage by administering an effective amount of the novel compositions to the skin of a mammal in need of such inhibition or protection.

U.S. Pat. Nos. 5,445,815 and 5,676,934, both to Siegfried, refer to powder-based UV-light screens. Powders comprise particles that are separated from one another by some distance. When applied to a surface, such as mammalian skin, powders do not form a uniform layer. That powders often comprise particles of non-uniform size exacerbates this problem. Accordingly, UV-light screens that are powder-based are less efficient that UV-light screens than those that form uniform layers when applied to a surface and, accordingly, provide relatively lower sun-protection factor ("SPF") values when applied to the skin. In addition, powders often impart an unpleasant, chalky texture to a surface. When applied to skin, especially where the user is exposed to sunlight, powders absorb perspiration and become "cakey," imparting an unpleasant sensation to the skin. Furthermore, powders are easily removed from the skin by washing or bathing, which also removes any UV-light screen contained in the powder.

U.S. Pat. No. 5,204,090 to Han relates to waterproof UV-light screening compositions that comprise water-insoluble ether solvents. Application of these types of ether-based formulations to the skin leaves a greasy film that is not only unpleasant to the touch, but that can also become "sticky," especially when admixed with perspiration, causing particles such as sand or dirt to adhere to the skin.

Accordingly, it is an object of the present invention to provide UV-light screens that overcome the above-mentioned disadvantages.

SUMMARY OF THE INVENTION

The present invention relates to anhydrous UV-light screen compositions comprising octocrylene, octyldodecyl neopentanoate, and a $C_1$–$C_4$ alcohol vehicle. Preferably, the $C_1$–$C_4$ alcohol vehicle comprises ethanol in an amount of preferably, at least about 95 percent by weight of the vehicle.

The present compositions can further comprise one or more fatty acid esters other than octyldodecyl neopentanoate. Preferably, the fatty acid ester is a benzyl ester of a $C_{12}$–$C_{16}$ acid. More preferably, the one or more fatty acid esters is a mixture of benzyl laurate, benzyl myristate, and benzyl palmitate that is sold by Alzo, Inc. under the trade name DERMOL B-246.

The present compositions can further comprise an acrylates/t-octylacrylamide copolymer. Preferably, the acrylates/t-octylacrylamide copolymer is that which is sold by National Starch and Chemical Co. under the trade name DERMACRYL 79.

The present compositions can still further comprise one or more UV light-absorbing compounds other than octocrylene. Preferably, the UV light-absorbing compound is 2-ethylhexyl p-methoxycinnamate. More preferably, the UV light-absorbing compounds are 2-ethylhexyl pmethoxycinnamate and oxybenzone.

The present compositions can still further comprise one or more silicones. Preferably the silicone is cyclomethicone.

The present compositions can still further comprise one or more additional ingredients.

The invention also relates to methods of inhibiting or preventing UV light-induced skin damage comprising administering an effective amount of a present composition to the skin of a mammal in need of such inhibition or prevention.

The phrases "alkyl," "alkenyl," and "alkynyl" include straight, branched, cyclic, or aryl carbon moieties.

The term "anhydrous," as used herein, unless otherwise indicated, means containing less than about 1 percent, by weight, of water, preferably less than about 0.5 percent, by weight, of water.

The term "(meth)acrylic acid," as used herein, unless otherwise indicated, means methacrylic acid or acrylic acid.

The phrase "pharmaceutically or cosmetically acceptable salt(s)," as used herein, unless otherwise indicated, includes salts of acidic or basic groups that may be present in compounds used in the present compositions. Compounds included in the present compositions that are basic in nature are capable of forming a wide variety of salts with various inorganic and organic acids. The acids that may be used to prepare pharmaceutically or cosmetically acceptable acid addition salts of such basic compounds are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e,. 1,1-methylene-bis-(2-hydroxy-3-naphthoate)) salts. Compounds included in the present compositions that include an amino moiety may form pharmaceutically or cosmetically acceptable salts with various amino acids, in addition to the acids mentioned above. Compounds, included in the present compositions, that are acidic in nature are capable of forming base salts with various pharmacologically or cosmetically acceptable cations. Examples of such salts include alkali metal or alkaline earth metal salts and, particularly, calcium, magnesium, sodium and potassium salts.

The phrase "pharmaceutically or cosmetically acceptable ester(s)," as used herein, unless otherwise indicated, includes acetate, succinate, palmitate, propionate, oleate, orotate, benzoate, p-aminobenzoate, p-nitrobenzoate, linoleate, nicotinate, 2-ethylhexanoate, and sorbate esters.

The term "sprayable," as used herein, unless otherwise indicated, is meant dispensable in atomized form.

Certain compounds of the present compositions may have asymmetric centers and therefore exist in different enantiomeric and diastereomic forms. This invention relates to the use of all optical isomers and stereoisomers of such compounds, and mixtures thereof, and to all pharmaceutical compositions and methods of treatment that may employ or contain them.

The present invention may be understood more fully by reference to the detailed description and illustrative examples which are intended to exemplify non-limiting embodiments of the invention.

DETAILED DESCRIPTION OF THE INVENTION

The present anhydrous compositions comprise octocrylene, octyldodecyl neopentanoate, and a $C_1$–$C_4$ alcohol vehicle.

Octocrylene, whose chemical name is 2-ethylhexyl-2-cyano-3,3-diphenyl-2-propenoate, can be synthesized via conventional organic chemical means or purchased commercially from, for example, Haarman & Reimer Corp. (Springfield, N.J.) under the trade name NEO HELIOPAN 303 or from BASF Corp; (Mount Olive, N.J.) under the trade name UVINUL N-539-SG. Octocrylene is present in the present compositions in an amount effective to provide UV-light screening when admixed with octyldodecyl neopentanoate. Such effective amount of octocrylene is from about 1 to about 15 weight percent, preferably from about 1 to about 5 weight percent, of the present compositions.

Octyldodecyl neopentanoate, also known as isoarachidyl neopentanoate (see U.S. Pat. No. 5,116,604 to Fogel et al.), can be prepared by condensing isoarachydyl alcohol with neopentanoic acid, or, preferably, obtained commercially from Bernel Chemical Co. (Englewood, N.J.) under the trade name ELEFAC 1-205. Octyldodecyl neopentanoate is present in the present compositions in an amount effective to enhance the UV-light screening ability of octocrylene. Such effective amount of octyldodecyl neopentanoate is from about 1 to about 50 weight percent, preferably from about 5 to about 25 weight percent, of the present compositions.

The $C_1$–$C_4$ alcohol vehicle solvates the octocrylene, octyldodecyl neopentanoate, and other optional ingredients. The $C_1$–$C_4$ alcohol used as the vehicle is an anhydrous alkanol or mixture of anhydrous alkanols of 14 carbon atoms, including methanol, ethanol, n-propanol, isopropanol, n-butanol, isobutanol, sec-butanol, t-butanol, and mixtures thereof. Preferably, the $C_1$–$C_4$ alcohol vehicle comprises ethanol, preferably in an amount of at least about 95 weight percent. More preferably, the $C_1$–$C_4$ alcohol vehicle is a mixture of ethanol and isopropanol, wherein the isopropanol is present in an amount of from about 5 weight percent or less by weight of the mixture. Such a mixture is sold by Pharmco Products, Inc. (Brookfield, Conn.) under the trade name ALCOHOL SDA 3-C, which is a mixture of about 95 weight percent ethanol and about 5 weight percent of isopropanol. Without being bound by any particular theory, Applicants believe that by virtue of the low molecular weight and high vapor pressure of the $C_1$–$C_4$ alcohol(s), the $C_1$–$C_4$ alcohol vehicle readily evaporates from the skin of a mammal when applied thereto, resulting in a uniform deposition of octocrylene and octyldodecyl neopentanoate. The amount of 14 alcohol vehicle ranges from about 10 to about 90 weight percent, preferably from about 25 to about 75 weight percent, of the present compositions.

The present compositions can further comprise one or more fatty acid esters other than octyldodecyl neopentanoate. Without being bound by any particular theory, Applicants believe that the incorporation of a fatty acid ester other than octyldodecyl neopentanoate helps to solvate the octocrylene, functions as an emollient, and/or enhances octocrylene's skin substantivity. Suitable fatty acid esters are $C_1$–$C_{20}$ alkyl, $C_2$–$C_{20}$ alkenyl, or $C_2$–$C_{20}$ alkynyl $C_2$–$C_{20}$ carboxylate esters. Suitable $C_1$–$C_{20}$ alkyl groups include methyl, ethyl, n-propyl, iso-propyl, n-butyl, iso-butyl, sec-butyl, t-butyl, n-pentyl, iso-pentyl, sec-pentyl, neopentyl, n-hexyl, iso-hexyl, sec-hexyl, phenyl, benzyl, n-heptyl, iso-heptyl, sec-heptyl, n-octyl, iso-octyl, sec-octyl, 2-ethylhexyl, t-octyl, nonyl, n-decyl, isodecyl, sec-decyl, n-undecyl, iso-undecyl, sec-undecyl, n-dodecyl, iso-dodecyl, sec-dodecyl, octyldodecyl, n-tridecyl, iso-tridecyl, sec-tridecyl, n-tetradecyl, iso-tetradecyl, sec-tetradecyl, n-pentadecyl, iso-pentadecyl, sec-pentadecyl, n-hexadecyl, iso-hexadecyl, sec-hexadecyl, n-heptadecyl, iso-heptadecyl, sec-heptadecyl, n-octadecyl, iso-octadecyl, sec-octadecyl, n-nonadecyl, iso-nonadecyl, sec-nonadecyl, n-eicosyl, iso-eicosyl, and sec-elcosyl. Suitable $C_2$–$C_{20}$ alkenyl groups include oleyl, linoleyl, and linolenyl. Suitable $C_2$–$C_{20}$ alkynyl groups include 2-propynyl, 3-butynyl, 4-pentynyl, 1,1-dimethylpropynyl, ω-hexinyl, propargyl, 2-methyl-4-pentynyl, ω-undecynyl, alkynyiphenyl, and 3-dodecynyl. Suitable $C_2$–$C_{20}$ carboxylate groups include butanoate, pentanoate, 2-methylpentanoate, 3-methylpentanoate, neopentanoate, 2,2-dimethylpropanoate, hexanoate, 2-methylhexanoate, 3-methylhexanoate, 4-methyihexanoate, 2-ethylbutanoate, 2,2-dimethylbutanoate, benzoate, heptanoate, 2-methylheptanoate, 3-methylheptanoate, 4-methyiheptanoate, 2-ethylhexanoate, octanoate, 2-methyloctanoate, 3-methyloctanoate, 4-methyloctanoate, nonanoate, 2-methylnonanoate, 3-methylnonanoate, 4-methylnonanoate, 5-methylnonanoate, 3,3,5-trimethylhexanoate, decanoate, 2-methyldecanoate, 3-methyldecanoate, 4-methyldecanoate, 5-methyldecanoate, undecanoate, dodecanoate, dineopentylacetate, methyl-t-butylneopentylacetate, tridecanoate, tetradecanoate, pentadecanoate, pentadecanoate, hexadecanoate, heptadecanoate, octadecanoate, 16-methylheptadecanoate, hydroxysterate, oleate, linoleate, linolenate, nonadecanoate, and eicosate.

Preferably, the one or more fatty acid esters other than octyldodecyl neopentanoate is tridecyl neopentanoate, isotridecyl isononanoate, isodecyl neopentanoate, isodecyl hydroxystearate, isodecyl laurate, isodecyl myristate, isodecyl oleate, isodecyl palmitate, decyl oleate, isocetyl palmitate, isohexadecyl isodecanoate, dodecyl benzoate, tridecyl benzoate, tetradecyl benzoate, pentadecyl benzoate, hexadecyl benzoate, benzyl neopentanoate, benzyl laurate, benzyl myristate, and benzyl palmitate, or mixtures thereof.

More preferably, the one or more fatty acid esters is a benzyl ester of $C_{12}$–$C_{16}$ acid, most preferably, a mixture of benzyl laurate, benzyl myristate, and benzyl palmitate, commercially available from Alzo, Inc. (Matawan, N.J.) and sold under the trade name DERMOL B-246. When present, the one or more fatty acid esters other than octyldodecyl neopentanoate is present in an amount of from about 1 to about 50 weight percent, preferably from about 5 to about 25 weight percent, of the present compositions.

The present compositions can further comprise an acrylates/t-octylacrylamide copolymer. The acrylates/t-octylacrylamide copolymer forms a film that, when included in the present compositions, incorporates octocrylene and octyldodecyl neopentanoate and increases the SPF values of the present compositions. The acrylates/t-octylacrylamide copolymer comprises repeat units of t-octylacrylamide and (meth)acrylic acid or a simple ester thereof and can be prepared by polymerization methods well known to those skilled in the art, for example, those disclosed in U.S. Pat. No. 5,736,125 to Morawsky et al., incorporated herein by reference. Preferably, the acrylates/t-octylacrylamide copolymer comprises (meth)acrylic acid repeat units; more preferably, it has a density of about 3.3 lbs/gal, a number average molecular weight of about 7500, a weight average molecular weight of about 96,000, and a glass transition temperature of about 103° C. Most preferably, the acrylates/t-octylacrylamide copolymer is that which is sold by National Starch and Chemical Co. under the trade name DERMACRYL 79. When present, the acrylates/t-octylacrylamide copolymer is present in an amount of from about 0.1 to about 10 weight percent, preferably from about 1 to about 5 weight percent, of the present compositions.

The present compositions can still further comprise one or more UV light-absorbing compounds other than octocrylene. The incorporation of one or more UV light-absorbing compounds in the present compositions help increase their SPF values. Useful UV light-absorbing compounds include p-aminobenzoic acid; p-dimethylaminobenzoic acid; anthranilates; o-aminobenzoates; salicylates; cinnamic acid derivatives such as α-phenyl cinnamonitrile, 2-ethylhexyl p-methoxycinnamate, and butyl cinnamoyl pyruvate; Dihydroxycinnamic acid derivatives such as umbelliferone, methylumbelliferone, and methylacetoumbelliferone trihydroxycinnamic acid derivatives such as esculetin, methylesculetin, daphnetin, and glucosides esculin and daphnin; hydrocarbons such as diphenylbutadiene and stilbene; dibenzalacetone benzalacetophenone, naphtholsulfonates such as 2-naphthol-3,6disulfonic and 2-naphthol-6,8-disulfonic acids; dihydroxynaphthoic acid; o- and p-hydroxybiphenyldisulfonates; coumarin derivatives such as 7-hydroxy-, 7-methyl-, and 3-phenylcoumarin; diazoles such as 2-acetyl-3-bromoindazole, phenyl benzoxazole, methyl naphthoxaxole, and various aryl benzothiazoles; quinine; quinoline derivatives such as 8-hydroxyquinoline and 2-phenylquinoline; hydroxy- or methoxy-substituted benzophenones; uric and vilouric acids; tannic acid and its derivatives (e.g., hexaethylether); (butylcarbityl) (6-propyl piperonyl) ether; hydroquinone; benzophenones such as oxybenzone, sulisobenzone, dioxybenzone, 2,2',4,4'-Tetrahydroxybenzophenone, 2,2'-Dihydroxy-4,4'-dimethoxybenzophenone, and octabenzone; benzoresorcinol 4-isopropyldibenzolymethane; butylmethoxydibenzoylmethane; etocrylene; and 4-isopropyl-di-benzoylmethane, pharmaceutically or cosmetically acceptable salts thereof; and esters thereof, including methyl, ethyl, menthyl, phenyl, benzyl, phenylethyl, linalyl, terpinyl, cyclohexenyl, isopropyl, isobutyl, 2-ethylhexyl, amyl, glyceryl, and dipropyleneglycol esters.

2-Ethyihexyl p-methoxycinnamate, oxybenzone, 4,4'-t-butyl methoxydibenzoylmethane, 2-hydroxy-4-methoxybenzophenone, octyl dimethyl p-aminobenzoic acid, diagalloyltrioleate, 2,2-dihydroxy-4-methoxybenzophenone, ethyl-4-[bis(hydroxypropyl)] aminobenzoate, 2-ethylhexyl-2-cyano-3,3-diphenylacrylate, 2-ethylhexyl-salicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl)-5-sulfonic-benzoxazoic acid and mixtures of these compounds, are particularly useful.

Preferably, the UV light-absorbing compound is 2-ethylhexyl p-methoxycinnamate. More preferably, the UV light-absorbing compounds are 2-ethylhexyl p-methoxycinnamate and oxybenzone. When present, the one or more UV light-absorbing compounds other than octocrylene is present in an amount of from about 1 to about 20 weight percent, preferably from about 1 to about 10 weight percent, of the present compositions.

The present compositions can still further comprise one or more silicones. The presence of a silicone can increase the waterproofing ability and skin substantivity of the present compositions. Useful silicones include cyclomethicone, cyclotetrasiloxane, cyclopentasiloxane, cyclohexasiloxane, a polydimethylsiloxane, an alkyldimethicone, a polyphenylmethylsiloxane such as a 15 phenyldimethicone or a phenyltrimethicone, octamethylcyclotetrasiloxane, decamethylcyclopentasiloxane, dodecamethylcyclohexasiloxane, hexamethyldisiloxane, dimethicone copolyol, dimethylpolysiloxane, diethylpolysiloxane, a mixed $C_1$–$C_3$ alkyl polysiloxane, and phenyldimethicone. Such silicones are commercially available from Dow Corning Corp. (Midland, Mich.). Preferably, the silicone is cyclomethicone, more preferably, cyclomethicone that is sold by Dow Coming Corp. under the trade name DOW CORNING 344 FLUID. When present, the one or more silicones is present in an amount of from about 5 to about 50 weight percent, preferably from about 10 to about 35 weight percent, of the present compositions.

The present compositions can still further comprise one or more additional ingredients.

For example, the present compositions can comprise one or more preservatives, such as an alkyl paraben, hydroquinone, citric acid, butylated hydroxytoluene, and butylated hydroxyanisole. Preferably, the one or more preservatives is a mixture of isopropylparaben, isobutylparaben, and butylparaben sold by ISP Sutton Laboratories (Chatham, N.J.) under the trade name LIQUAPAR OIL. When present, the one or more preservatives is present in an amount of from about 0.01 to about 0.5 weight percent of the present compositions.

The present compositions can also comprise one or more naturally-occurring compounds such as candellilla wax, α-bisabolol, aloe vera, aloe barbadensis extract, eucalyptus globulus extract, guava extract, Matricaria extract, cocoa extract, palm kernel oil, lanolin, Manjistha extract, and Guggal extract. When present, the one or more naturally-occurring compounds is present in an amount of from about 0.01 to about 0.5 weight percent of the present compositions. A useful composition containing octyl palmitate, aloe barbadensis extract, eucalyptus globulus extract, guava extract, matricaria extract, cocoa extract, palm kernel oil, and lanolin is sold by Active Organics (Van Nuys, Calif.) under the trade name ACITPLEX 336 LIPO OP.

The present compositions can comprise one or more vitamins, including retinol (Vitamin A), dehydroretinol (Vitamin $A_2$), cyanocobalamin (Vitamin $B_{12}$), calciferol (Vitamin $D_2$), 1:1 lumisterol:Vitamin $D_2$(Vitamin $D_1$), colecalciferol (Vitamin $D_3$), 22,23-dihydroergocalciferol (Vitamin $D_4$), tocopherol (Vitamin E), 3-phytylmenadione (Vitamin $K_1$), menaquinones (Vitamin(s) $K_2$), 1-hydroxy-2-methyl-4-aminonaphthalene (Vitamin $K_5$), 1,4-diamino-2-methylnaphthalene (Vitamin $K_6$), 1-amino-2-methyl-4-naphthol (Vitamin $K_7$), S-(2-methyl-1,4-naphthoquinonyl-3)-β-mercaptopropionic acid (Vitamin K-S(II)), tetrahydro-3,4-dihydroxy-5-methylmercaptomethyl)-2-furyl)adenine (Vitamins L), tegotin (Vitamin T), methylmethioninesulfonium chloride (Vitamin U), a pharmaceutically or cosmetically acceptable salt thereof, and a pharmaceutically or cosmetically acceptable ester thereof. Preferably, the vitamins are tocopherol acetate, more preferably, tocopherol acetate that is sold by Hoffman-LaRoche (Nutley, N.J.); and Vitamin A palmitate, more preferably Vitamin A palmitate that is sold by BASF Corp. (Mount Olive, N.J.). When present, the one or more vitamins is present in an amount of from about 0.01 to about 0.5 weight percent of the present composition.

The present compositions can additionally comprise one or more perfumes or fragrances. A useful fragrance is that sold by Firmenich Inc. (Princeton, N.J.) under the trade name FRAGRANCE 49.073/T. When present, the one or more perfumes or fragrances is present in an amount of from about 0.1 to about 1 weight percent of the present compositions.

The present compositions can additionally comprise dihydroxyacetone ("DHA"), either in its monomeric or dimeric form, or as a mixture of monomeric and dimeric forms. DHA can be used as an artificial tanning agent. When present, dihydroxyacetone is present in an amount of from about 0.1 to about 20 percent by weight of the present compositions.

The present compositions can comprise additional ingredients including abrasives, absorbents, antiacne agents, anticaking agents, antifoaming agents, antimicrobial agents, antioxidants, binders, biological additives, buffering agents, bulking agents, chelating agents, chemical additives, colorants, cosmetic astringents, cosmetic biocides, denaturants, drug astringents, emulsion stabilizers, external analgesics, film formers, fragrance components, humectants, opacifying agents, propellants, reducing agents, skin bleaching agents, skin-conditioning agents (emollients, humectants, miscellaneous, and occlusive), skin protectants, surfactants (cleansing agents, emulsifying agents, foam boosters, hydrotropes, solubilizing agents, suspending agents, and nonsurfactants), viscosity decreasing agents, and viscosity increasing agents.

In a preferred embodiment, the present compositions comprise: (a) octocrylene, in an amount of from about 1 to about 15 weight percent; (b) octyldodecyl neopentanoate, in an amount of from about 1 to about 50 weight percent; (c) a $C_1$–$C_4$ alcohol vehicle, in amount of from about 10 to about 90 weight percent; (d) one or more fatty acid esters other than octyldodecyl neopentanoate, the one or more fatty acid esters being in an amount of from about 1 to about 50 weight percent; (e) an acrylates/t-octylacrylamide copolymer, in an amount of from about 0.1 to about 10 weight percent; (f) one or more UV light-absorbing compounds other than octocrylene, the one or more UV light-absorbing compounds being present in an amount of from about 1 to about 20 weight percent; and (g) one or more silicones, in an amount of from about 5 to about 50 weight percent, of the present compositions.

In a more preferred embodiment, the present compositions comprise: (a) octocrylene, in an amount of from about 1 to about 5 weight percent; (b) octyldodecyl neopentanoate, in an amount of from about 5 to about 25 weight percent; (c) a $C_1$–$C_4$ alcohol vehicle, in an amount of from about 25 to about 75 weight percent; (d) one or more fatty acid esters other than octyldodecyl neopentanoate, the one or more fatty acid esters being in an amount of from about 5 to about 25 weight percent; (e) an acrylates/t-octylacrylamide copolymer, in an amount of from about 1 to about 5 weight percent; (f) one or more UV light-absorbing compounds other than octocrylene, the one or more UV light-absorbing compounds being present in an amount of from about 1 to about 10 weight percent; and (g) one or more silicones, in an amount of from about 10 to about 35 weight percent, of the present compositions.

In a still more preferred embodiment, the $C_1$–$C_4$ alcohol vehicle comprises ethanol, the one or more fatty acid esters other than octyldodecyl neopentanoate is DERMOL B-246, the acrylates/t-octylacrylamide copolymer is DERMACRYL 79, the one or more UV light-absorbing compounds other than octocrylene is 2-ethylhexyl p-methoxycinnamate, and the silicone is cyclomethicone. In a most preferred embodiment, the $C_1$–$C_4$ alcohol vehicle comprises ethanol, the one or more fatty acid esters other than octyldodecyl neopentanoate is DERMOL B-246, the acrylates/t-octylacrylamide copolymer is DERMACRYL 79, the one or more UV light-absorbing compounds other than octocrylene are 2-ethylhexyl p-methoxycinnamate and oxybenzone, and the silicone is cyclomethicone.

The present compositions can be prepared by admixing their components in no particular order. Where the present compositions comprise an acrylates/t-octylacrylamide copolymer or a silicone, however, the acrylates/t-octylacrylamide copolymer or silicone is preferably added to the $C_1$–$C_4$ alcohol vehicle prior to adding the other components. In this case, the acrylates/t-octylacrylamide copolymer or silicone is slowly added to the $C_1$–$C_4$ alcohol vehicle at a temperature of from about room temperature to about 40° C., preferably at about room temperature, and mixed at the addition temperature for about 5 minutes to about one hour, preferably for about 15 minutes to about 45 minutes, or until a clear solution is obtained. Where the present compositions comprise both an acrylates/t-octylacrylamide copolymer and a silicone, the acrylates/t-octylacrylamide copolymer is preferably added to the $C_1$–$C_4$ alcohol vehicle prior to adding the silicone, which is added after a clear solution of acrylates/t-octylacrylamide copolymer and $C_1$–$C_4$ alcohol vehicle is obtained.

Octyldodecyl neopentanoate is added to the $C_1$–$C_4$ alcohol vehicle or to the $C_1$–$C_4$ alcohol vehicle solution of acrylates/t-octylacrylamide copolymer and/or silicone as described above for the addition of acrylates/t-octylacrylamide copolymer and/or silicone. Where the present compositions comprise one or more fatty acid esters other than octyldodecyl neopentanoate, it is preferable that a mixture of octyldodecyl neopentanoate and the fatty acid ester(s) is added to the $C_1$–$C_4$ alcohol vehicle or to the $C_1$–$C_4$ alcohol vehicle solution of acrylates/t-octylacrylamide copolymer and/or silicone as described above.

Next, octocrylene is added, as described above for the addition of acrylates/t-octylacrylamide copolymer and/or silicone, to the $C_1$–$C_4$ alcohol vehicle solution of octyldodecyl neopentanoate, which optionally contains acrylates/t-octylacrylamide copolymer, silicone, and/or fatty acid ester(s). Where the present compositions comprise one or more UV light-absorbing compounds other than octocrylene, it is preferable that a mixture of octocrylene and the one or more UV light-absorbing compounds is added, as described above for the addition of acrylates/t-octylacrylamide copolymer and/or silicone, to the $C_1$–$C_4$ alcohol vehicle solution of octyldodecyl neopentanoate.

Where the present compositions comprise one or more additional ingredients, each additional ingredient can be added separately to the $C_1$–$C_4$ alcohol vehicle solution of octyldodecyl neopentanoate and octocrylene, or, preferably, as a mixture of additional ingredients. In either case, the one or more additional ingredients are added to the $C_1$–$C_4$ alcohol vehicle solution of octyldodecyl neopentanoate and octocrylene as described above for the addition of acrylates/t-octylacrylamide copolymer and/or silicone.

The invention further relates to a method of inhibiting or preventing UV-light-induced skin damage comprising administering an effective amount of a present composition to the skin of a mammal, e.g., a human, a domestic pet, livestock, or other mammal, in need of such inhibition or prevention. The present compositions may be topically spread over the skin or may be rubbed into the skin to enhance penetration. Preferably, the compositions of the invention are applied in an amount of from about 0.1 to about 100 milligrams per $cm^2$ of skin; more preferably, from about 1 to about 5 milligrams per $cm^2$ of skin. The compositions are applied prior to or during exposure to UV light. For chronic exposure to UV light, the present compositions are applied at least once per day, preferably up to 8 times per day. The compositions may be applied up to about 4 hours prior to UV exposure, preferably up to about 2 hours prior to UV exposure.

By virtue of their $C_1$–$C_4$ alcohol vehicle, the present compositions have a viscosity that is low enough to render them sprayable, for example, from a pressurized or unpressurized spray bottle. The unpressurized spray bottle contains the present compositions in its fluid reservoir and can comprise a pump head and a dip tube connected to the pump head that extends into the liquid reservoir. Here, the present compositions are dispensed from the spray bottle by actuating the pump head. Alternatively, the unpressurized spray bottle can be fabricated from a resilient material such as a rubber, plastic, or other suitable elastomer and comprise a spray head or narrow orifice through which the present compositions can be dispensed by exerting pressure, preferably manually, on the unpressurized spray bottle.

Pressurized spray bottles include conventional aerosol spray containers comprising an air, hydrocarbon, or halocarbon propellant; a pressurized fluid dispenser as described in U.S. Pat. No. 4,964,540 to Katz, incorporated herein by reference in its entirety; and, preferably, a continuous dispensing system sold by Exxel Corp. (Somerset, N.J.) under the trade name ATMOS.

The following Examples further illustrate the compositions and methods of the present invention. It is to be understood that the present invention is not limited to the specific details of the Examples provided below.

EXAMPLE 1

Composition A was prepared as follows: 544.50 g of ALCOHOL SDA 3-C, 200 Proof (Pharmco Products, Inc., Brookfield, Conn.) were moderately agitated in a cleaned, sanitized, and water-free mixing vessel, such as a 1,500–2,000 ml glass beaker, and to it was added 10.00 g of DERMACRYL 79 (National Starch and Chemical Co., Bridgewater, N.J.). The resulting mixture was mixed at room temperature (approximately 22° C.) for approximately 30 minutes; then, 180.00 g of cyclomethicone (Dow Coming Corp., Midland, Mich.) were added. Agitation was maintained until a clear solution was obtained in about 5 minutes. A mixture of 100.00 g of ELEFAC 1-205 (Bernel Chemical Co., Inc., Englewood, N.J.) and 100.00 g of DERMOL B-246 (Alzo Inc., Matawan, N.J.) was added, and agitation of the resulting mixture was maintained until a clear solution was maintained in about 5 minutes. Then, a mixture of 30.00 g of 2-ethylhexyl p-methoxycinnamate (Haarman & Reimer Corp., Springfield, N.J.) and 20.00 g of octocrylene (Haarman & Reimer Corp., Springfield, N.J.) was added, and the resulting mixture was allowed to mix until a clear solution was obtained in about 5–10 minutes. Then, a mixture of 3.00 g of LIQUAPAR OIL (ISP Sutton Laboratories, Chatham, N.J.), 1.00 g of racemic α-bisabolol (BASF Corp., Mount Olive, N.J.), 3.00 g of tocopheryl acetate (Hoffman-LaRoche, Inc., Nutley, N.J.), 1.00 g of Vitamin A palmitate 1.7 Mio 1.U./g, unstabilized (BASF Corp., Mount Olive, N.J.), 2.50 g of ACTIPLEX 336 LIPO OP (Active Organics, Van Nuys, Calif.), and 5.00 g of Fragrance 49.073/T (Firmenich, Inc., Princeton, N.J.) was added, and the resulting mixture was mixed for approximately thirty minutes.

EXAMPLE 2

Composition B was prepared as follows: 504.50 g of ALCOHOL SDA 3-C, 200 Proof (Pharmco Products, Inc., Brookfield, Conn.) were moderately agitated in a cleaned, sanitized, and water-free mixing vessel, such as a 1,500–2,000 ml glass beaker, and to it was added 10.00 g of DERMACRYL 79 (National Starch and Chemical Co., Bridgewater, N.J.). The resulting mixture was mixed at room temperature for approximately 30 minutes; then, 180.00 g of cyclomethicone (Dow Corning Corp., Midland, Mich.) were added. Agitation was maintained until a clear solution was obtained in about 5 minutes. A mixture of 100.00 g of ELEFAC 1-205 (Bernel Chemical Co., Inc., Englewood, N.J.) and 100.00 g of DERMOL B-246 (Alzo Inc., Matawan, N.J.) was added, and agitation of the resulting mixture was maintained until a clear solution was maintained in about 5 minutes. Then, a mixture of 50.00 g of 2-ethylhexyl p-methoxycinnamate (Haarman & Reimer Corp., Springfield, N.J.), 10.00 g of oxybenzone (Haarman & Reimer Corp., Springfield, N.J.) that was manually crushed into smaller particles, and 30.00 g of octocrylene (Haarman & Reimer Corp., Springfield, N.J.) was added, and the resulting mixture was allowed to mix until a clear solution, free of undissolved solids, was obtained in about 30 minutes. Then, a mixture of 3.00 g of LIQUAPAR OIL (ISP Sutton Laboratories, Chatham, N.J.), 1.00 g of racemic α-bisabolol (BASF Corp., Mount Olive, N.J.), 3.00 g of tocopheryl acetate (Hoffman-LaRoche, Inc., Nutley, N.J.), 1.00 g of Vitamin A palmitate 1.7 Mb 1.U./g, unstabilized (BASF Corp., Mount Olive, N.J.), 2.50 g of ACTIPLEX 336 LIPO OP (Active Organics, Van Nuys, Calif.), and 5.00 g of Fragrance 49.0731T (Firmenich, Inc., Princeton, N.J.) was added, and the resulting mixture was mixed for approximately thirty minutes.

EXAMPLE 3

The SPF value of Composition B was determined using the protocol described in the U.S. Food and Drug Administration's Tentative Final Monograph, "Sunscreen Drug Products for Over-the-Counter Human Drugs" (Federal Register, Vol. 58, No. 90, pp. 28194–28302, 1993) (the "TFM"). More than 20 subjects were evaluated to determine the minimal erythema dose ("MED") values for unprotected skin and for skin protected with Composition B. A series of 1 $cm^2$ sites on the unprotected skin of each subject's back were exposed to different doses of radiation produced by a 150 watt Xenon Arc Solar Simulator (290 nm to 700 nm radiation) and measured using a Model DCS-1 Sunburn UV Meter/Dose Controller System. The varying doses of radiation were administered over a geometrical series of timed intervals, wherein each exposure time interval was 25% longer than the previous time. Reactions to radiation exposure were scored according to the following scale:

0=no reaction—no erythema.

0.5=very slight reaction—slight erythema—at least 25% of the exposure site, very faint but definitely pink.

1=mild reaction—minimal macular erythema, faint but definitely pink, usually the entire exposure site.

2=moderate reaction—moderate macular erythema, definite redness, sunburn; possible edema.

3=strong to severe reaction—intense redness, sunburn; probable edema, possible spreading The smallest dose of energy that produced redness reaching the borders of the exposure site and occurring 22 to 24 hours after exposure was determined as each individual's inherent MED ("MED(US)"). Composition B and an 8% homosalate standard were spread manually and uniformly with a glass rod over several 50 cm² areas on individuals' backs at a dose of 2 mg/cm². A series of radiation doses were administered to the protected skin and the smallest dose of energy that produced redness reaching the borders of the exposure site and occurring 22 to 24 hours after exposure was determined as the MED for skin protected by Composition B ("MED(PS)"). The SPF value of Composition B was obtained by calculating the ratio of MED(PS)/MED (US). The mean SPF and standard deviation (s) were calculated using data from the subjects. The SPE value obtained for Composition B was 8.

EXAMPLE 4

The SPF value of Composition A is evaluated according to the protocol of Example #3, above, as used for Composition B. The SPE value of Composition A will be 4.

EXAMPLE 5

Composition B's water resistance was determined using the protocol described in the TFM. More than 20 subjects were administered with Composition B as described in Example #3 and immersed for four 20-minute periods, with a 20-minute rest between each immersion period, in a fresh-water whirlpool maintained at 23–32° C. The SPF value of Composition B that remained on the subjects following immersion was determined, as above, and compared to that obtained prior to immersion as described in Example 3. The SPF value of Composition B that remained on the subjects following immersion was comparable to that obtained prior to immersion, demonstrating that Composition B is "very water resistant" as defined in the TEM.

EXAMPLE 6

Composition A's water resistance is evaluated according to the protocol of Example 5, above, as used for Composition B. Composition A will be "very water resistant" as defined in the TFM.

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

All references disclosed herein are hereby incorporated by reference in their entirety.

What is claimed is:

1. An anhydrous ultraviolet light screening composition, comprising octocrylene, octyldodecyl neopentanoate, and a $C_1$–$C_4$ alcohol vehicle.

2. The composition of claim 1, wherein the octocrylene is present in an amount of from about 1 to about 15 weight percent of the composition.

3. The composition of claim 1, wherein the octyldodecyl neopentanoate is present in an amount of from about 1 to about 50 weight percent of the composition.

4. The composition of claim 1, wherein the $C_1$–$C_4$ alcohol vehicle is present in an amount of from about 10 to about 90 weight percent of the composition.

5. The composition of claim 1, wherein the $C_1$–$C_4$ alcohol vehicle comprises ethanol.

6. The composition of claim 1, further comprising one or more fatty acid esters other than octyldodecyl neopentanoate, the one or more fatty acid esters being present in an amount of from about 1 to about 50 weight percent of the composition.

7. The composition of claim 6, wherein the fatty acid ester is a benzyl ester of a $C_{12}$–$C_{16}$ carboxylic acid.

8. The composition of claim 6, wherein the one or more fatty acid esters is DERMOL B-246.

9. The composition of claim 1, further comprising an acrylates/t-octylacrylamide copolymer present in an amount of from about 0.1 to about 10 weight percent of the composition.

10. The composition of claim 9, wherein the acrylates/t-octylacrylanlide copolymer is DERMACRYL 79.

11. The composition of claim 1, further comprising one or more UV-light absorbing compounds other than octocrylene, the one or more UV-light absorbing compounds being present in an amount of from about 1 to about 20 weight percent of the composition.

12. The composition of claim 11, wherein the UV-light-absorbing compound is 2-ethylhexyl p-methoxycinnamate.

13. The composition of claim 11, wherein the UV-light-absorbing compounds are 2-ethylhexyl p-methoxycinnamate and oxybenzone.

14. The composition of claim 1, further comprising one or more silicones present in an amount of from about 5 to about 50 weight percent of the composition.

15. The composition of claim 14, wherein the silicone is cyclomethicone.

16. An anhydrous ultraviolet light screening composition, comprising:
(a) octocrylene present in an amount of from about 1 to about 15 weight percent of the composition;
(b) octyldodecyl neopentanoate present in an amount of from about 1 to about 50 weight percent of the composition;
(c) a $C_1$–$C_4$ alcohol vehicle present in an amount of from about 10 to about 90 weight percent of the composition;
(d) one or more fatty acid esters other than octyldodecyl neopentanoate, the one or more fatty acid esters being present in an amount of from about 1 to about 50 weight percent of the composition;
(e) an acrylates/t-octylacrylanlide copolymer present in an amount of from about 0.1 to about 10 weight percent of the composition;
(f) one or more UV-light-absorbing compounds other than octocrylene, the one or more UV light-absorbing compounds being present in an amount of from about 1 to about 20 weight percent of the composition; and
(g) one or more silicones present in an amount of from about 5 to about 50 weight percent of the composition.

17. An anhydrous ultraviolet light screening composition, comprising:
(a) octocrylene present in an amount of from about 1 to about 15 weight percent of the composition;
(b) octyldodecyl neopentanoate present in an amount of from about 1 to about 50 weight percent of the composition;
(c) ALCOHOL SDA 3-C present in an amount of from about 10 to about 90 weight percent of the composition;
(d) DERMOL B-246 present in an amount of from about 1 to about 50 weight percent of the composition;
(e) DERMACRYL 79 present in an amount of from about 0.1 to about 10 weight percent of the composition;
(f) 2-ethyl hexyl p-methoxycinnamate present in an amount of from about 1 to about weight percent of the composition; and (g) cyclomethicone present in an amount of from about 5 to about 50 weight percent of the composition.

18. A method for inhibiting or preventing UV-light-induced skin damage comprising administering to the skin of a mammal in need of such inhibition or prevention an effective amount of the composition of claim 1.

19. The method of claim 18, wherein:

(a) the octocrylene is present in an amount of from about 1 to about 15 weight percent of the composition;

(b) the octyldodecyl neopentanoate is present in an amount of from about 1 to about 50 weight percent of the composition; and (c) the $C_1$–$C_4$ alcohol vehicle is present in an amount of from about 10 to about 90 weight percent of the composition, and further comprising:

(d) one or more fatty acid esters other than octyldodecyl neopentanoate, the one or more fatty acid esters being present in an amount of from about 1 to about 50 weight percent of the composition;

(e) an acrylates/t-octylacrylaniide copolymer present in an amount of from about 0.1 to about 10 weight percent of the composition;

(f) one or more UV-light-absorbing compounds other than octocrylene, the one or more UV light-absorbing compounds being present in an amount of from about 1 to about 20 weight percent of the composition; and (g) one or more silicones present in an amount of from about 5 to about 50 weight percent of the composition.

20. The method of claim 19, wherein:

(a) the one or more fatty acid esters is DERMOL B-246;

(b) the acrylates/t-octylacrylamide copolymer is DERMACRYL 79;

(c) the UV-light-absorbing compound is 2-ethylhexyl p-methoxycinnamate; and (d) the silicone is cyclomethicone.

\* \* \* \* \*